(12) United States Patent
Williams, III et al.

(10) Patent No.: US 7,632,275 B2
(45) Date of Patent: Dec. 15, 2009

(54) ORTHOPEDIC REAMER

(75) Inventors: Philip F. Williams, III, Teaneck, NJ (US); Christopher DeMaria, Glen Rock, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 324 days.

(21) Appl. No.: 10/882,759

(22) Filed: Jul. 1, 2004

(65) Prior Publication Data
US 2006/0004371 A1 Jan. 5, 2006

(51) Int. Cl.
*A61B 17/00* (2006.01)
(52) U.S. Cl. .......................... 606/80; 408/227
(58) Field of Classification Search ............. 606/79–81, 606/86, 160, 167, 170, 180, 86 R; 30/351–353, 30/356, 346.53–346.55; 408/227, 229, 231; 144/20–24
See application file for complete search history.

(56) References Cited

U.S. PATENT DOCUMENTS

| 1,089,527 | A | * | 3/1914 | Bolton | 407/41 |
|---|---|---|---|---|---|
| 1,332,455 | A | * | 3/1920 | Auble | 408/156 |
| 1,422,988 | A | * | 7/1922 | Raymund | 407/44 |
| 1,483,950 | A | * | 2/1924 | Peterson | 408/164 |
| 1,579,102 | A | * | 3/1926 | Gale | 408/167 |
| 1,923,177 | A | | 8/1933 | Tucker | |
| 2,423,419 | A | * | 7/1947 | Stuber | 407/38 |
| 3,702,611 | A | * | 11/1972 | Fishbein | 606/81 |
| 3,977,398 | A | | 8/1976 | Burstein | |
| 4,135,847 | A | | 1/1979 | Hemmings | |
| 5,417,696 | A | | 5/1995 | Kashuba et al. | |
| 5,653,712 | A | * | 8/1997 | Stern | 606/80 |
| 5,755,719 | A | * | 5/1998 | Frieze et al. | 606/81 |
| 5,839,897 | A | | 11/1998 | Bordes | |
| 5,993,455 | A | | 11/1999 | Noble | |
| 6,015,408 | A | | 1/2000 | Pichon et al. | |
| 6,055,731 | A | * | 5/2000 | Zucker | 30/49 |
| 6,139,508 | A | * | 10/2000 | Simpson et al. | 600/564 |
| 6,168,599 | B1 | * | 1/2001 | Frieze et al. | 606/80 |
| 6,332,886 | B1 | | 12/2001 | Green et al. | |
| 6,383,188 | B2 | * | 5/2002 | Kuslich et al. | 606/80 |

(Continued)

FOREIGN PATENT DOCUMENTS

FR 2 847 453 A 5/2004

OTHER PUBLICATIONS

The Complete Injection Molding Process (27 pages).
Design of Plastic Parts for Appearance, Strenth and Longevity in Medical Applications. Mehta, Kishor S., Bayer Corporation (3 pages).
European Search Report for EP Application No. 052908, Dated Aug. 11, 2005.

*Primary Examiner*—Thomas C Barrett
*Assistant Examiner*—James L. Swiger
(74) *Attorney, Agent, or Firm*—Lerner, David, Littenberg, Krumholz & Mentlik, LLP

(57) ABSTRACT

An orthopedic reamer for use in creating and sizing canals in a bone is disclosed. The orthopedic reamer includes a non-polymeric cutting portion having at least one cutting surface thereon and a polymeric body portion covering at least a portion of the cutting portion. The at least one cutting surface is not covered by the polymeric body portion.

22 Claims, 16 Drawing Sheets

U.S. PATENT DOCUMENTS

| | | |
|---|---|---|
| 6,517,581 B2 | 2/2003 | Blamey |
| 6,780,175 B1* | 8/2004 | Sachdeva et al. ............ 604/531 |
| 2003/0097133 A1 | 5/2003 | Green et al. |
| 2003/0153943 A1* | 8/2003 | Michael et al. ............. 606/200 |
| 2004/0049199 A1* | 3/2004 | Lechot et al. ................. 606/80 |
| 2004/0215197 A1* | 10/2004 | Smith et al. ................... 606/79 |
| 2004/0260291 A1* | 12/2004 | Jensen ........................ 606/69 |
| 2005/0113826 A1* | 5/2005 | Johnson et al. ............... 606/45 |

\* cited by examiner

ORTHOPEDIC REAMER

FIELD OF THE INVENTION

The present invention relates to orthopedic reamers for use in creating and sizing canals in a bone and, more particularly, to an orthopedic reamer that has been designed to permit the use of low-cost manufacturing methods while being durable and still maintaining its ability to create such canals.

BACKGROUND OF THE INVENTION

Many surgical procedures call for the precise and accurate reaming of bone material. For example, during a total hip arthroplasty, the diameter of the femoral canal must be widened in order to be capable of receiving a femoral stem. In the total hip procedure, a reamer can approximate a portion of the femoral implant geometry and can impart this shape on the femoral canal. Both of these functions are required in order to provide a satisfactory interface between the femoral hip implant and the remaining bone.

Typically, an orthopedic reamer, or set of reamers of varying diameters and lengths, is utilized to increase the diameter of the canal in a bone. This is generally done on long bones within the body, but can be done on any bone suitable for the reaming process. Normally, the canal is progressively reamed in 1 or 2 mm increments until the desired diameter is reached. Examples of reamers of this type are shown in U.S. Pat. No. 6,168,599 to Frieze et al. and U.S. Pat. No. 6,162,226 to DeCarlo, Jr., et al.

While orthopedic reamers such as those described above are capable of creating or increasing the diameter of canals in a bone, they have their shortcomings. Most importantly, the manufacturing costs associated with orthopedic reamers have traditionally been high. A standard reamer is typically constructed of a metallic or other hard material machined from a solid block or rod or from several solid pieces that are assembled to form the reamer. These high costs have required such reamers to be utilized in multiple procedures. This reuse requires the cleaning and sterilization of such a reamer before each use, which adds significant additional costs. Improper cleaning and sterilization can lead to disease transmission. Furthermore, multiple uses of a reamer create the greater probability of failure due to fatigue and/or poor cutting due to wear of the cutting surfaces of the reamer. Hence, a disposable single use orthopedic reamer would be advantageous.

For the foregoing reasons, there is a need for a reamer that can be inexpensively manufactured and suitable for single use, while maintaining the required precise and accurate dimensions needed for reaming a bone.

SUMMARY OF THE INVENTION

A first aspect of the present invention is an orthopedic reamer comprising an non-polymeric cutting portion having at least one bone cutting surface thereon and a polymeric body portion covering at least a portion of the cutting portion, wherein the at least one bone cutting surface is not covered by the polymeric body portion.

Another embodiment of the present invention is an orthopedic reamer having at least two metal blade portions, each blade portion having at least one outwardly extending cutting surface, the blade portions oriented at an angle to adjacent blade portions forming a recess therebetween and a polymeric support at least partially filling the recesses between the blades, the polymeric support leaving the cutting surfaces exposed.

Another aspect of the present invention is a method of making an orthopedic reamer comprising the steps of providing at least one non-polymeric section having at least one bone cutting surface thereon; and injection molding a polymeric body portion over at least a portion of the at least one non-polymeric section. The at least one bone cutting surface remains uncovered by the polymeric body portion.

Yet another aspect of the present invention is a reamer kit comprising at least two different sized orthopedic reamers, each of the orthopedic reamers including a non-polymeric cutting portion having at least one blade with a bone cutting surface thereon and a polymeric body portion covering at least a portion of the bone cutting portion, wherein the at least one bone cutting surface is not covered by the polymeric body portion. Furthermore, the reamer kit may be packaged, either sterilely or non-sterilely, with other instruments, such as trial or replacement stem implants, trial or replacement head implants, trial or replacement implants used for sizing different lengths and angles, broaches, saws, and any other instrument or implant typically utilized in an orthopedic surgical procedure.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

In describing the preferred embodiments of the subject matter illustrated and to be described with respect to the drawings, specific terminology will be resorted to for the sake of clarity. However, the invention is not intended to be limited to the specific term and includes all technical equivalence which operate in a similar manner to accomplish a similar purpose.

As used herein, the term "distal" means more distant from the heart and the term "proximal" means closest to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
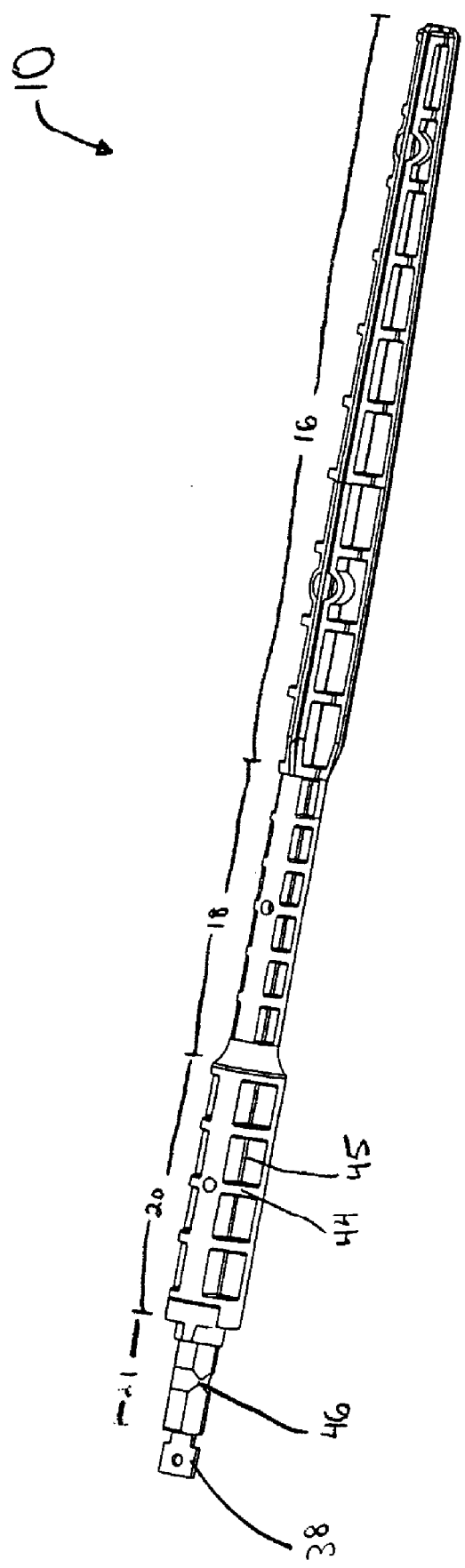
FIG. 1 is a side perspective view of the orthopedic reamer according to an embodiment of the present invention.
Figure 2:
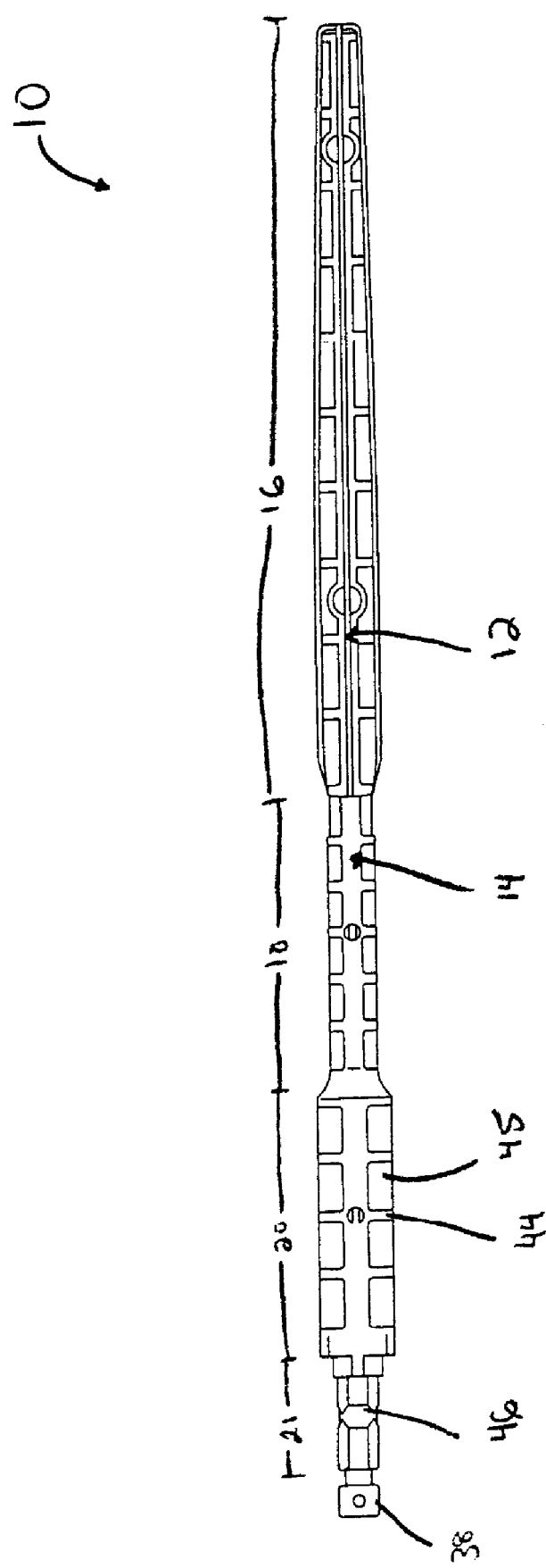
FIG. 2 is a side plan view of the reamer according to FIG. 1.

Referring to the drawings, wherein like reference numerals represent like elements, there is shown in the Figures, in accordance with embodiments of the present invention, an orthopedic reamer designated generally by reference numeral 10. In a preferred embodiment, reamer 10 is designed to be used in reaming the proximal end of the femur, more particularly the femoral canal. However, it is contemplated that other embodiments of the present invention can be utilized in conjunction with reaming other bones capable of being reamed such as the tibia and the humerus. A preferred embodiment reamer 10, shown in FIGS. 1 and 2, includes a non-polymeric cutting portion 12 and a polymeric body portion 14. Cutting portion 12 and body portion 14 are configured so that reamer 10 includes four sections: cutting section 16, intermediate section 18, base section 20, and end section 21. Each of the sections 16, 18, 20, and 21 are of a different size (i.e.—a different diameter). Furthermore, in certain embodiments cutting section 16 may be tapered (i.e.—having varying diameters along its length). However, it is contemplated that reamer 10 can be configured in any manner suitable for reaming a bone, including additional or fewer sections and configured with different dimensions and shapes.

Preferred cutting portion 12 comprises two cutting components 13a and 13b (best shown in FIGS. 3-6). However, it is contemplated that other embodiments may include only one component or multiple components. Each component is constructed of a metal, but can be any other rigid material. In a preferred completed reamer 10, cutting portion 12 is partially enveloped by body portion 14. This is typically accomplished by injection molding any high strength, biocompatible engineering polymer such as ULTEM® over cutting components 13a and 13b. It should be noted however, that other materials can be utilized. For example, polyetherimide, polyimide, polyethersulfone, polyphenylsulfone, polycarbonate, polymethylmethacrylate, any fiber filled variation of these polymers, any amorphous polymeric material, or any other bio-compatible injection moldable polymer.

Figure 3:
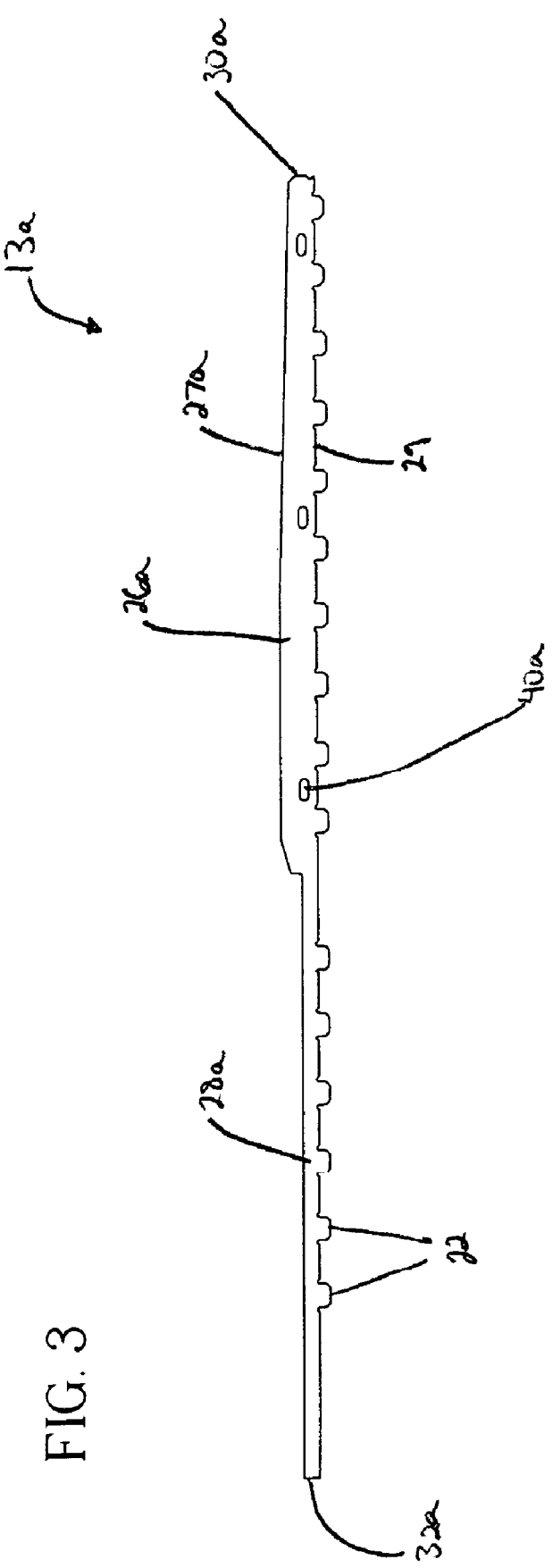
FIG. 3 is a side plan view of a first cutting component of the reamer according to FIG. 1.
Figure 15:
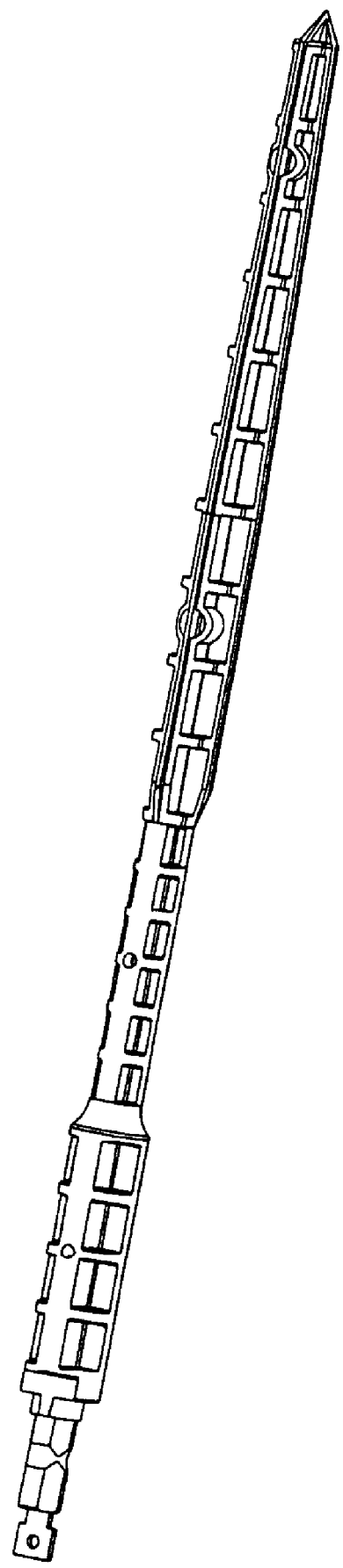
FIG. 15 is a side perspective view of the orthopedic reamer having a pointed tip according to another embodiment of the present invention.
Figure 16:
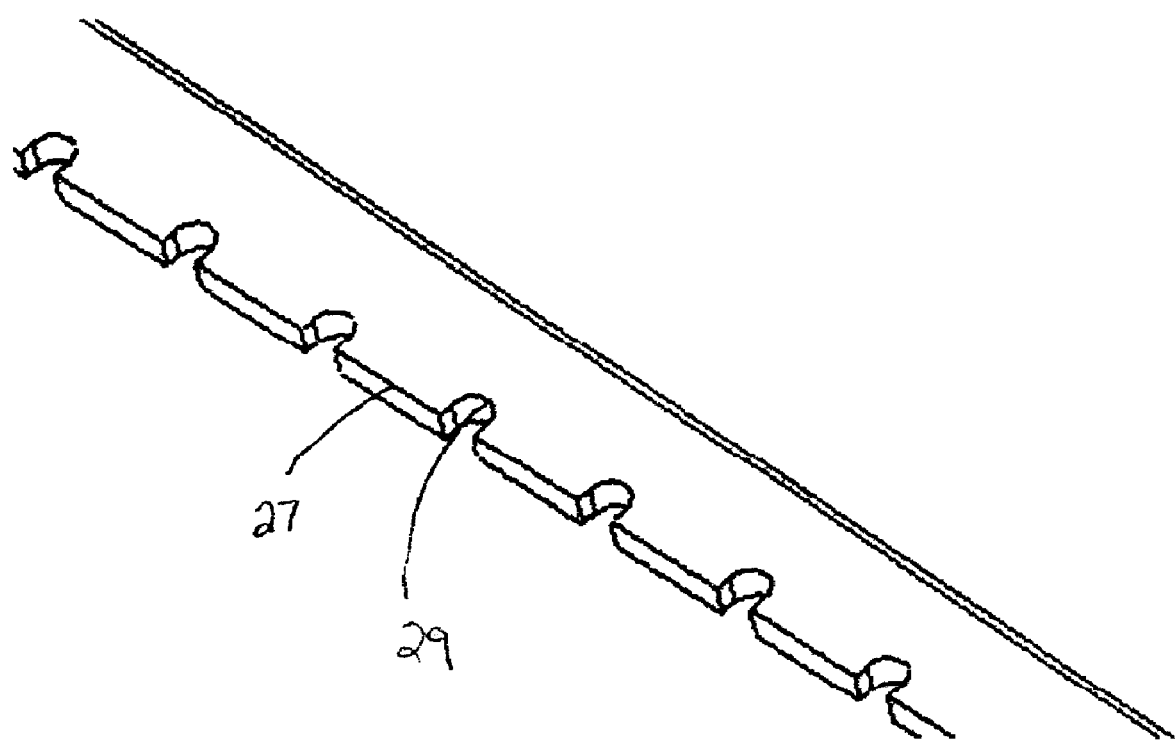
FIG. 16 is a perspective enlarged view of a cutting surface of the orthopedic reamer showing a plurality of chip breakers.

Cutting portion 12 is the infrastructure and foundation for the completed reamer 10. As shown in FIGS. 3-6, cutting components 13a and 13b provide the structure needed to create the aforementioned sections i.e., cutting section 16, intermediate section 18, base section 20, and end section 21 of reamer 10. In a preferred embodiment, cutting component 13a, as shown in FIG. 3, includes bone cutting surface or blade portion 26a, intermediate surface 28a, blade tip 30a, and end 32a. Blade portion 26a is essentially an extended surface, which is wider than the other surfaces of cutting component 13a. In a preferred embodiment, blade portion 26a includes a sharp edge 27a for facilitating the cutting of a bone. It is contemplated that one or more chip breakers 29 (shown in FIG. 16) can be included along sharp edge 27a. In a preferred embodiment, chip breaker 29 is a relief or void in blade portion 26a and sharp edge 27a, which allows for newly cut bone to be transported from the canal while reamer 10 remains therein. In the preferred embodiment shown in FIG. 1, intermediate surface 28a resides along the remainder of cutting component 13a from blade portion 26a to end 32a. This section extends less in the radial direction, i.e., is narrower than blade portion 26a. Blade tip 30a is located at the termination point of cutting surface 26a, at the side of blade portion 26a opposite to end 32a. This tip surface 30a is the first surface of cutting component 13a that is capable of making contact with a bone surface. In the embodiment shown in FIGS. 3-6, blade tip 30a is substantially flat. However, it is contemplated that blade tip 30a can be pointed, especially in embodiments utilized to initialize a canal in a bone. This is shown in FIG. 15.

Figure 4:
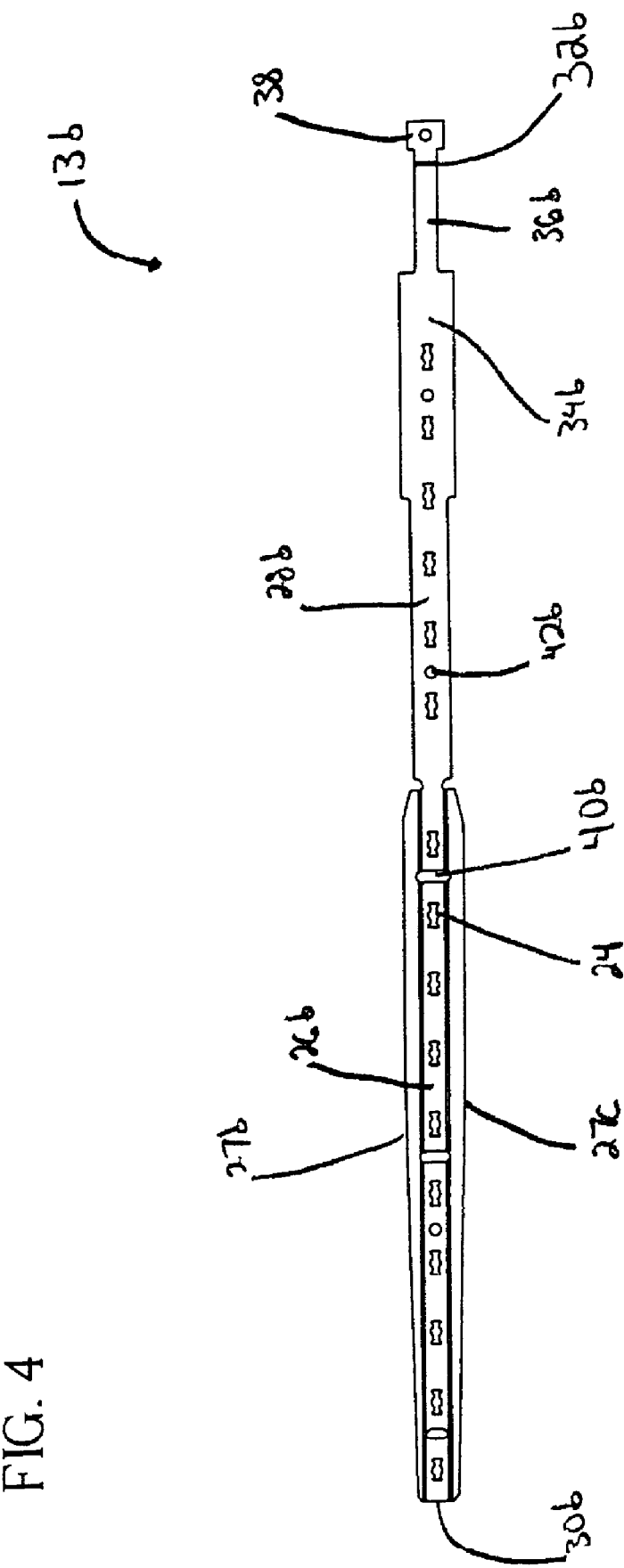
FIG. 4 is a top plan view of a second cutting component of the reamer according to FIG. 1.
Figure 5:
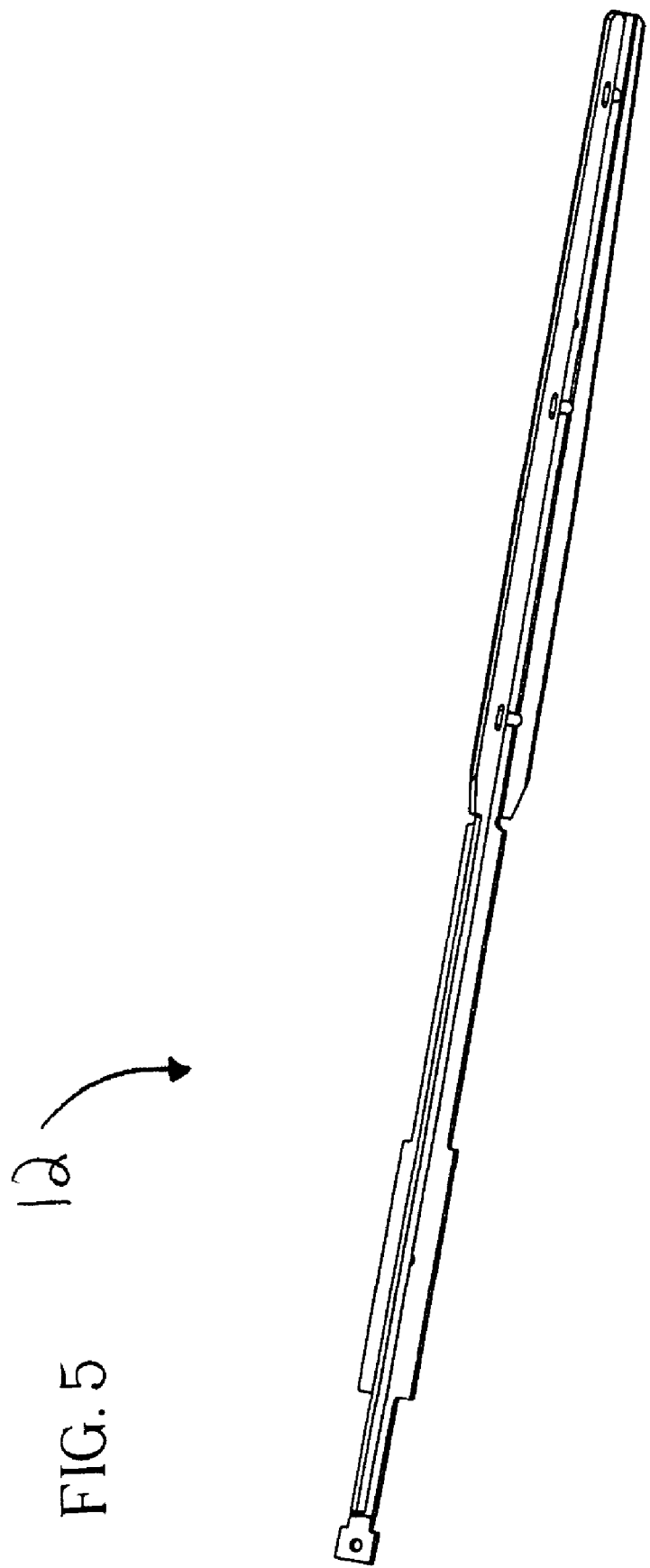
FIG. 5 is a perspective view of the cutting components of FIGS. 3 and 4 assembled together.

As is also best shown in FIG. 4, cutting component 13b includes bone cutting surface or blade portion 26b, intermediate surface 28b, blade tip 30b, end 32b, base surface 34b, end surface 36b, and mold alignment tab 38. Blade portion 26b, like blade portion 26a, has essentially an extended surface that is wider than the other surfaces of cutting component 13b. In a preferred embodiment, blade portion 26b includes sharp edges 27b and 27c, located on opposing sides of blade portion 26b, which facilitate the cutting of a bone. The two sharp edges 27b and 27c provide a second and third cutting edge (when taken in combination with sharp edge 27a). It is contemplated that one or more chip breakers 29 (shown in FIG. 16), like that discussed above in relation to cutting component 13a, can also be included for use with sharp edges 27b and 27c. In the preferred embodiment, sharp edges 27b and 27c extend from blade portion 26b in an angular fashion. This is best shown in cross-sectional FIG. 7, and will be discussed more fully below. Intermediate surface 28b is connected to blade portion 26b on one end, and is narrower than blade portion 26b. Base surface 34b is connected to and is wider than intermediate surface 28b. In a preferred embodiment, base surface 34b is not as wide as blade portion 26b, however it is contemplated that it can be of any width narrower than that of blade portion 26b. End surface 36b is connected to and is narrower than base surface 34b. Blade tip 30b is located at the termination point of blade portion 26b, at a side of cutting surface 26b that is opposite to end 32b. This tip surface 30b is the first surface of cutting component 13b capable of making contact with a bone surface. In the embodiment shown in FIGS. 3-6, tip surface 30b is substantially flat. However, like that of blade tip 30a, it is contemplated that blade tip 30b can be pointed, especially in embodiments utilized to initialize a canal in a bone (shown in FIG. 15). It should be noted that when cutting bone blade tips 30a and 30b work in conjunction with one another, and should be configured so as to compliment each other. Finally, in the preferred embodiment, cutting component 13b includes mold alignment tab 38 (best shown in FIG. 4) connected to end surface 36b. Mold alignment tab 38 facilitates easy connection to a mold utilized in the injection molding of reamer 10. This will be discussed further below. In a preferred embodiment, mold alignment tab 38 is easily removable from cutting component 13b, and is removed subsequent to the injection molding process.

Figure 6:
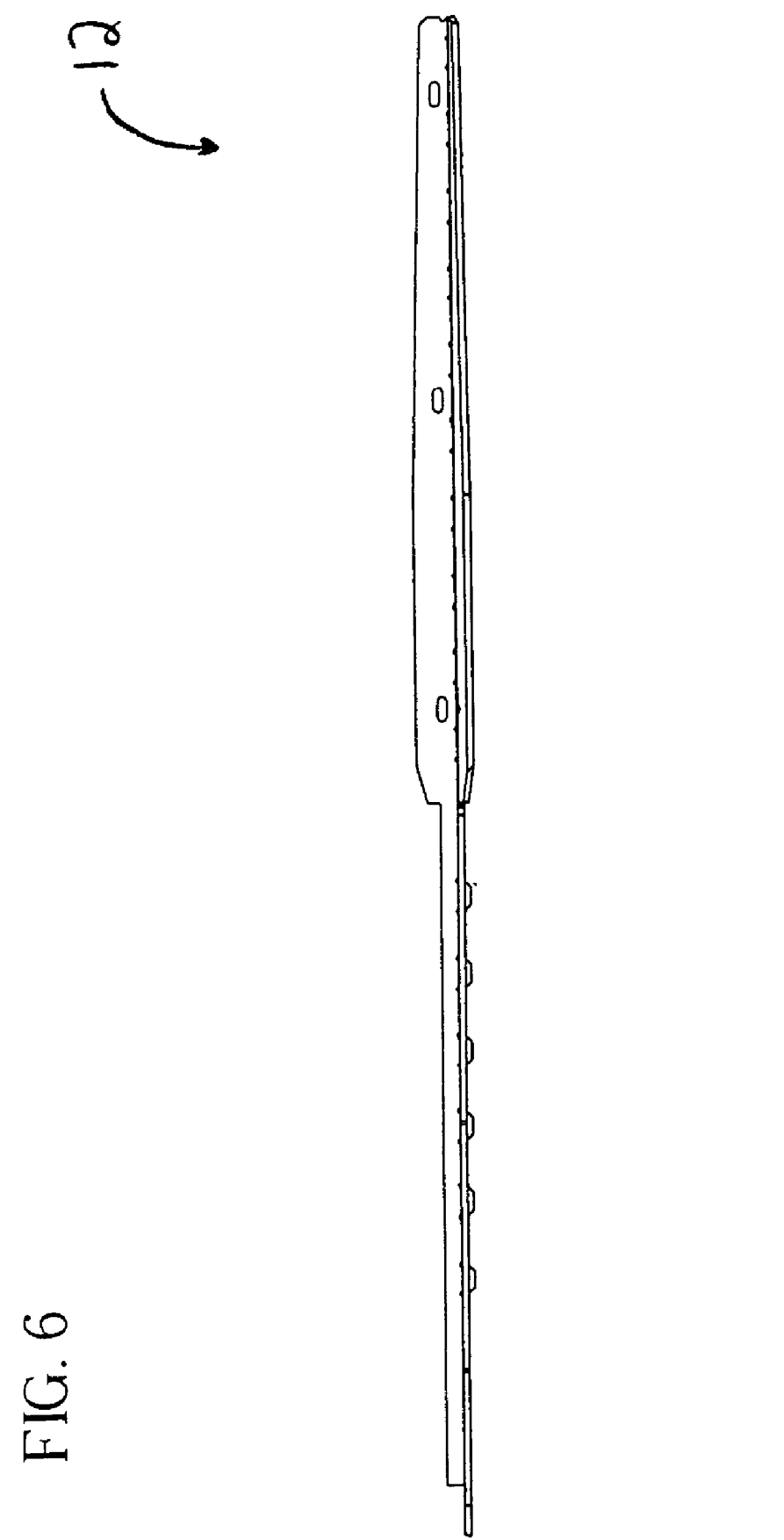
FIG. 6 is a side plan view of the cutting component of FIGS. 3 and 4 assembled together.

Cutting component 13a also includes a plurality of tabs 22 and cutting component 13b includes a plurality of slots 24. Preferably, slots 24 and tabs 22 are sized to interlock. During assembly, cutting components 13a and 13b connect and may be retained together because of the mating of tabs 22 and slots 24. The configuration of the two elements essentially allows for tabs 22 to be staked into slots 24. This is best shown in FIG. 6. A preferred embodiment of the present invention includes sixteen pairs of tabs 22 and slots 24. However, it is contemplated that any number of tabs 22 and slots 24 can be utilized in the construction of the cutting components 13a and 13b. Furthermore, tabs 22 and slots 24 can be of any shape or design for facilitating connection between cutting components 13a and 13b. In a preferred embodiment, the aforementioned tabs 22 extend outwardly from both blade portion 26a and intermediate surface 28a of cutting component 13a, and the aforementioned slots 24 lie on blade portion 26b, intermediate surface 28b, and base surface 34b of cutting component 13b. However, it is contemplated that tabs 22 and slots 24 can be located on any of the surfaces of the cutting components 13a and 13b.

The preferred embodiment includes cutting portion 12 and body portion 14 molded around cutting portion 12. This polymeric body portion 14 is injection molded substantially around cutting portion 12, in accordance with processes that would be known to one or ordinary skill in the art. Essentially, cutting portion 12 provides a strong core for reamer 10 that runs along its entire length. Polymeric body portion 14 further reinforces this structure and, in addition, provides a finished look to reamer 10. To allow for the polymeric material to cool evenly and eliminate shrinkage subsequent to the injection molding process, body 14 includes a plurality of ribbed sections 44. These ribbed sections 44 create voids 45 in body portion 14 (best shown in FIGS. 1 and 2), thereby also reducing the amount of polymeric material required and axiomatically lowering the overall weight of reamer 10. However, ribbed sections 44 are designed so that polymeric body portion 14 remains a strong reinforcement for cutting portion 12. It is contemplated that various configurations for ribbed sections 44 can be utilized. Similarly, a solid surfaced polymeric body portion 14 can be formed. However, the aforementioned problems solved by providing the ribbed sections may occur during molding.

In a preferred embodiment depicted in the Figures, cutting portion 12 also includes first elongated apertures 40a located on cutting section 13a, second elongated apertures 40b located on cutting section 13b, and circular apertures 42b located on cutting section 13b. These apertures are provided on the given cutting component to allow polymer material to flow from one side of 13a and 13b to the other during the injection molding of polymeric body portion 14. It is contemplated that any number or any shaped holes can be included on the cutting sections 13a and 13b. It is also contemplated that such apertures are not required, but rather improve the connection between cutting portion 12 and body portion 14. In a preferred embodiment, each cutting component 13a and 13b is constructed from a metallic material suitable for inserting into the body, such as stainless steel, and is manufactured through stamping. However, cutting components 13a and 13b can be of any material suitable for facilitating the reaming of a bone, and can be manufactured from any process known to one of ordinary skill in the art.

Figure 7:
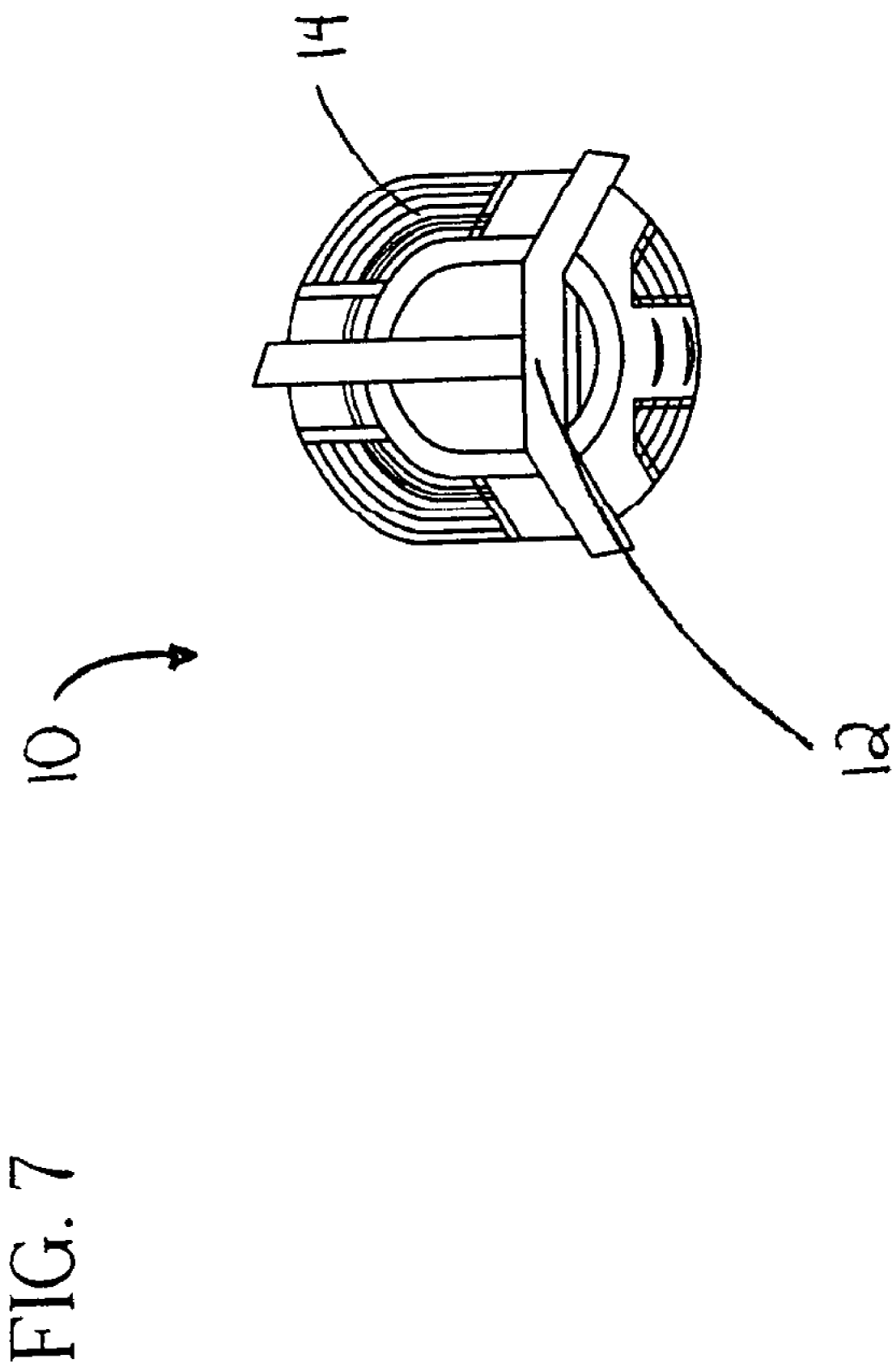
FIG. 7 is a cross sectional view of the cutting section of reamer according to FIG. 1 taken at the tip portion.

In a preferred completed form of reamer 10, sharp edges 27a, 27b, and 27c, and blade tips 30a and 30b are not covered by polymeric material (best shown in FIG. 7). Polymeric body portion 14 is filled between the recesses formed between sharp edges 27a, 27b, and 27c, but does not cover the edges. This allows such surfaces to directly contact a bone surface, when reamer 10 is brought into engagement with a bone. The remaining surfaces of cutting portion 12 are substantially covered by the polymeric material of body portion 14, in the fully constructed reamer 10. Therefore, in its fully constructed form, the exterior surface of reamer 10 is completely polymeric material in intermediate section 18, base section 20, and end section 21.

Polymeric body portion 14 is typically molded to the various sections of reamer 10 to create a substantially circular cross-section. It is contemplated that reamer 10 may be of any cross-sectional shape. However, the circular cross section of cutting section 16 shown in FIG. 7 is advantageous for allowing reamer 10 to be rotated. Furthermore, the alignment of sharp edges 27a, 27b, and 27c provide for a balanced reamer 10, upon rotation during cutting. The angularity of sharp edges 27b and 27c allows the three edges to be situated 120 degrees from one another in a preferred embodiment. This alignment balances reamer 10, decreases the amount of chatter in such upon rotation, and provides a self centering reamer with three points of contact. In a preferred embodiment, intermediate section 18, base section 20, and end section 21 all also have substantially circular cross-sections.

Figure 10:
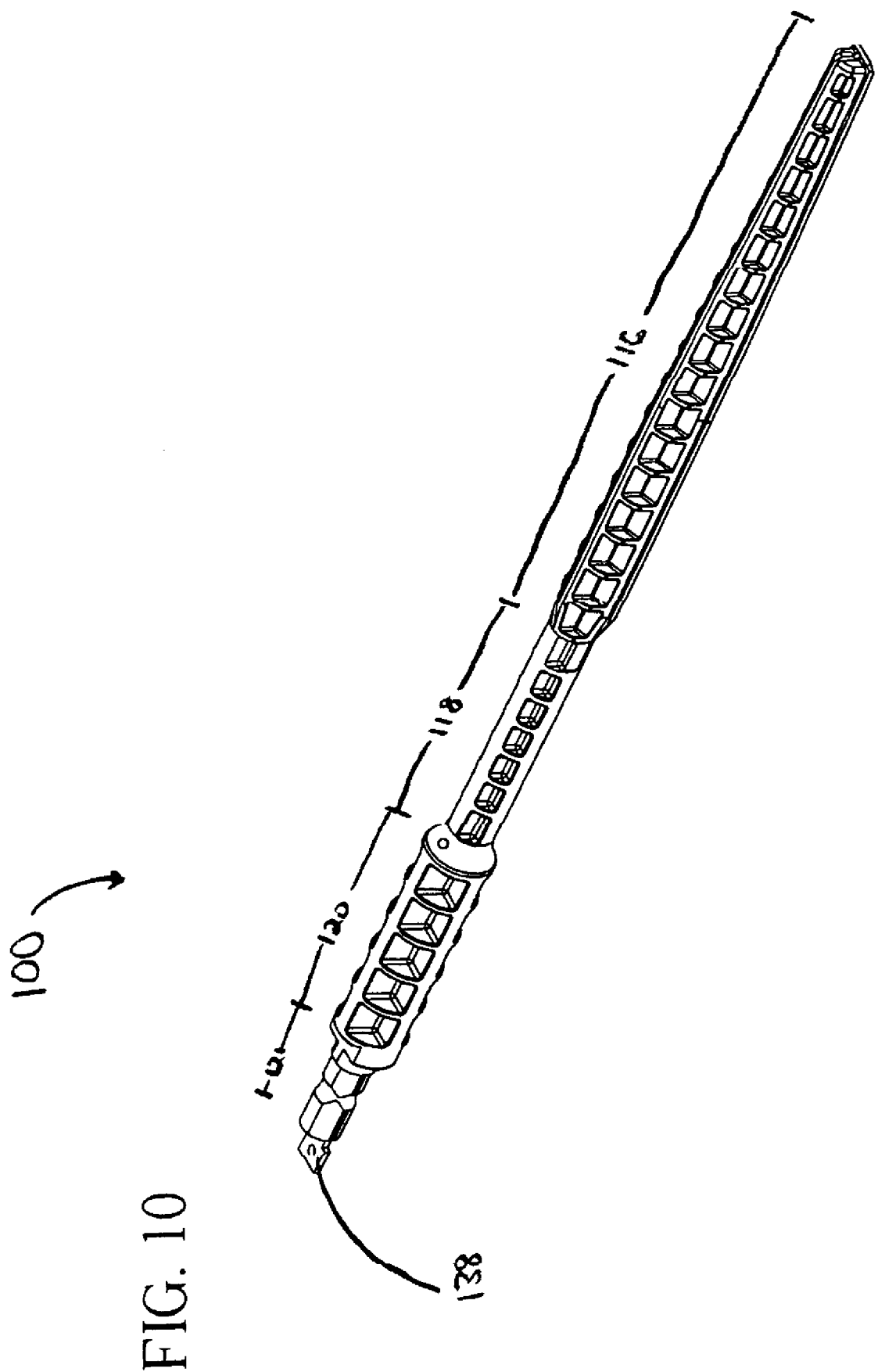
FIG. 10 is a perspective view of the orthopedic reamer according to another embodiment of the present invention.

Other embodiments, like that shown in FIG. 10, may not include a substantially circular cross section in all sections of the reamer. Reamer 100, as shown in FIG. 10, includes a generally non-circular cross section in cutting section 116. This flows from the fact that cutting section 116 of reamer 100 includes three sharp edges 127a, 127b, and 127c arranged such that one edge is positioned ninety degrees to the other two, thereby creating the triangular-like cross-section. It is also contemplated that other embodiments may include a plurality of sharp edges ranging from one to six, arranged to form any shaped cross section. For example, an embodiment that includes four sharp edges could allow for a circular cross-section. Another embodiment may include a single sharp edge.

In a preferred embodiment (shown in FIGS. 1 and 2), base section 20 and end section 21 are molded with polymeric material such that their configuration facilitates easy connection to a drive device, such as a drill. It is contemplated that such a connection can be accomplished by various means known to one of ordinary skill in the art. The embodiment shown in FIG. 1 includes a quick connection 46. This quick connection 46 is configured so as to mate with a female connection (not shown) of a drive device. While the quick connection 46 is shown to have an exterior surface substantially constructed of polymeric material, it is contemplated that other embodiments may be constructed in a manner similar to cutting section 16, i.e. metallic portions of cutting portion 12 may extend outwardly with no polymeric material located thereon. A design of this type would allow for any direct mating between quick connection 46 and a metallic female connection to be a metal on metal mating.

Figure 11:
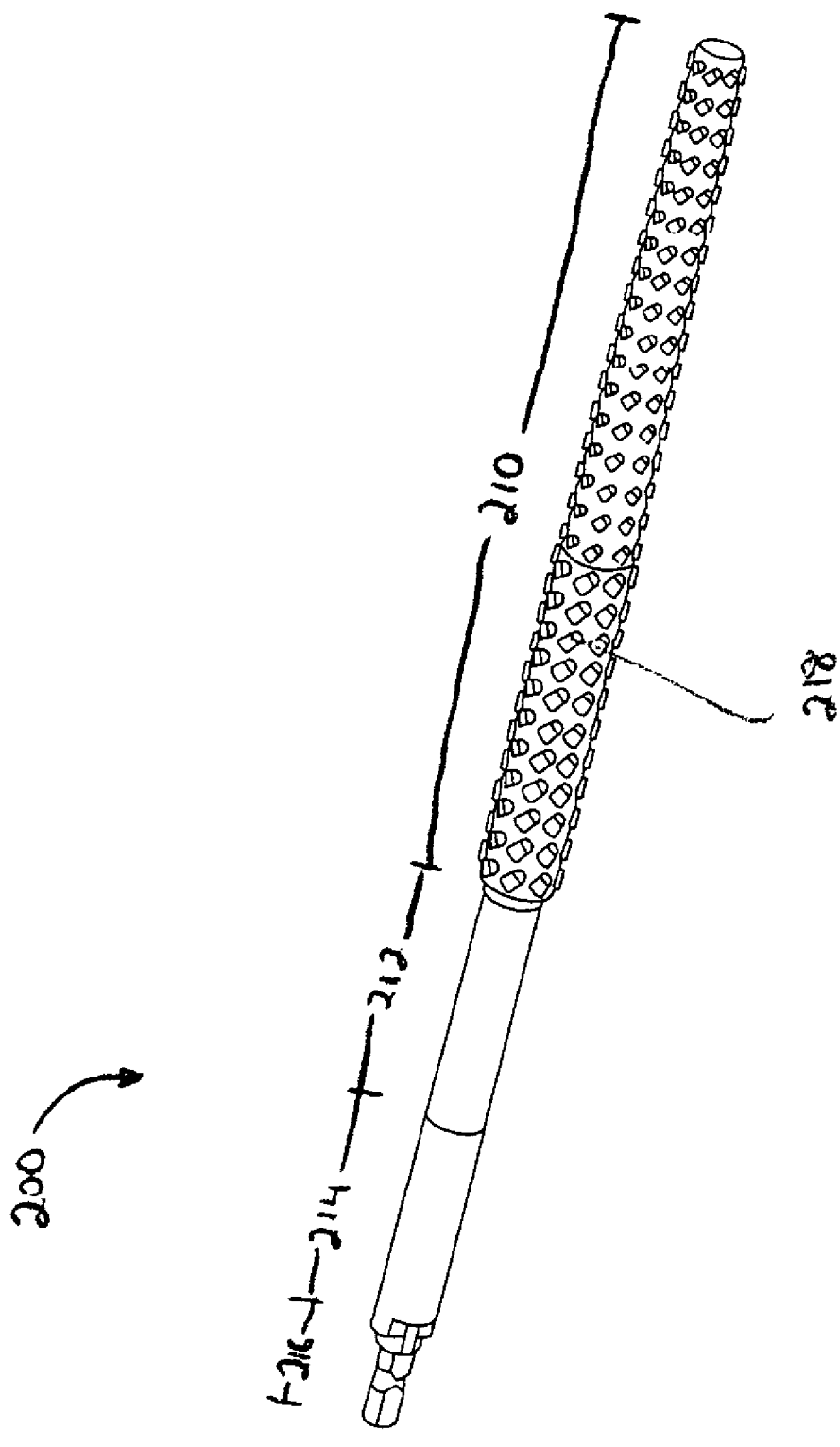
FIG. 11 is a perspective view of the orthopedic reamer according to another embodiment of the present invention.

Another embodiment, shown in FIG. 11, includes a reamer 200 having a cutting section 210, an intermediate section 212, a base section 214, and an end section 216, like that of reamer 10. Also like that of reamer 10, reamer 200 includes a metallic core created from cutting components, which is surrounded by a polymeric body section. However, reamer 200 includes a cheese grater like configuration instead of cutting surfaces or blades. Cutting section 210 of reamer 200 includes a plurality of cutting teeth 218, for facilitating the cutting of a bone. This cutting section 210 is a sheet of metal with cutting teeth 218 formed thereon. In its completed form, reamer 200 is shaped similar to that of reamer 10. However, the sheet of metal with cutting teeth 218 formed thereon is wrapped around cutting section 210. Thereafter, sheet of metal can be connected in a manner known in the art, for example through welding or a mechanical connection such as a tab and slot configuration. It is contemplated that cutting section 210 can have an exterior surface of either polymeric or metallic material. The sheet of metal can be fixed to either material. Furthermore, it is contemplated that the metallic core of reamer 200 can be hollow and the sheet metal portion can have several apertures, thereby allowing for resected bone material to be captured within reamer 200.

Figure 12:
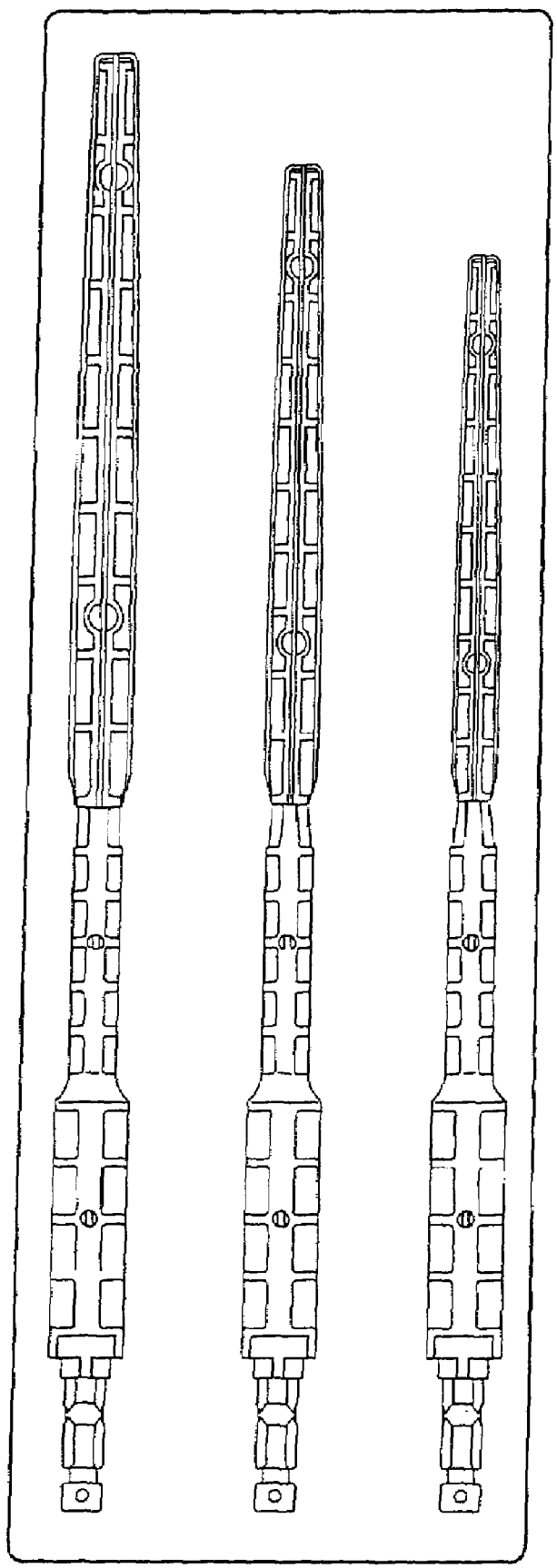
FIG. 12 is a top plan view of a kit of orthopedic reamers according to an embodiment of the present invention.
Figure 13:
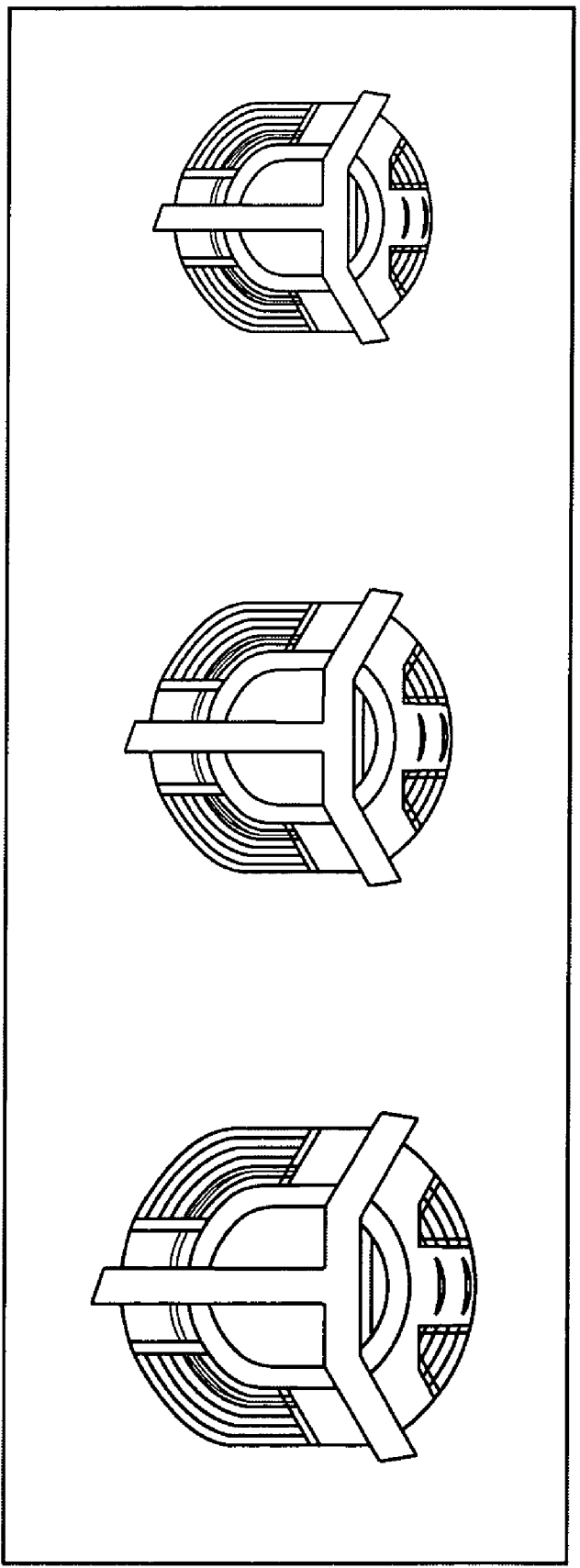
FIG. 13 is a cross sectional view of a kit of orthopedic reamers according to an embodiment of the present invention.
Figure 14C:
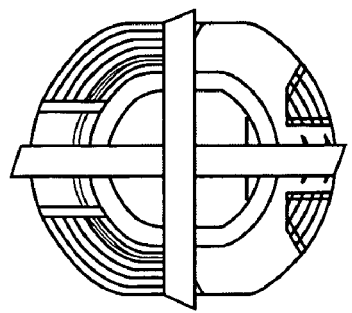
FIGS. 14A-14F show cross sectional views of reamers having different numbers of blades.
Figure 14F:
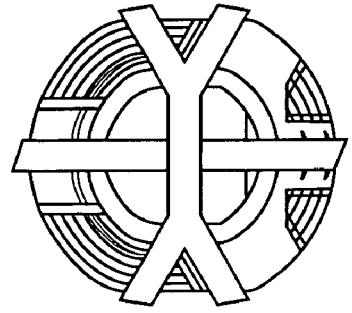
Figure 14B:
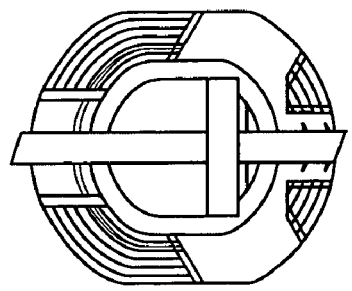
Figure 14E:
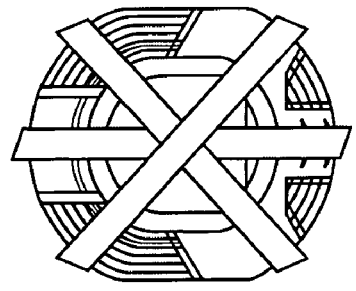
Figure 14A:
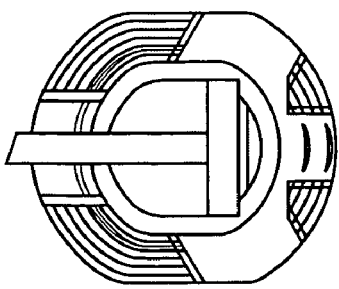
Figure 14D:
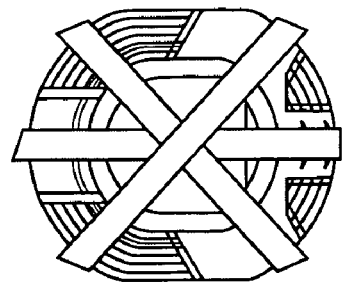

In other embodiments, a kit may be provided which includes two or more reamers in accordance with the present invention. Examples of kits of this type are shown in FIGS. 12 and 13. Typically, a surgical procedure, such as that relating to a total hip arthroplasty, will require the enlargement of a canal diameter. In most cases, a surgeon will utilize several orthopedic reamers, of increasing diameters, to achieve the desired canal diameter. It is contemplated that two, three, or more reamers 10, of varying diameters, in accordance with the present invention may be provided in an orthopedic kit. Such a kit may include a package or case and other tools necessary for performing the desired procedure. In certain embodiments, it would be advantageous to provide several sterile varying sized reamers 10 each or all in a sterile package. Such a kit would prevent the need for individually sterilizing each instrument prior to surgery, and given the disposable nature of reamer 10, would allow for all instruments to be discarded thereafter. In certain embodiments, a kit may include a reamer having a pointed tip for facilitating the creation of a canal, in addition to other sized reamers. A kit of this type may be desirable for use in procedures that require the initiation of holes or canals in a bone. Furthermore, the reamer kit may be packaged, either sterilely or non-sterilely, with other instruments, such as trial or replacement stem implants, trial or replacement head implants, trial or replacement implants used for sizing different lengths and angles, broaches, saws, spacer blocks, pins, and any other instrument or implant typically utilized in an orthopedic surgical procedure.

Figure 8:
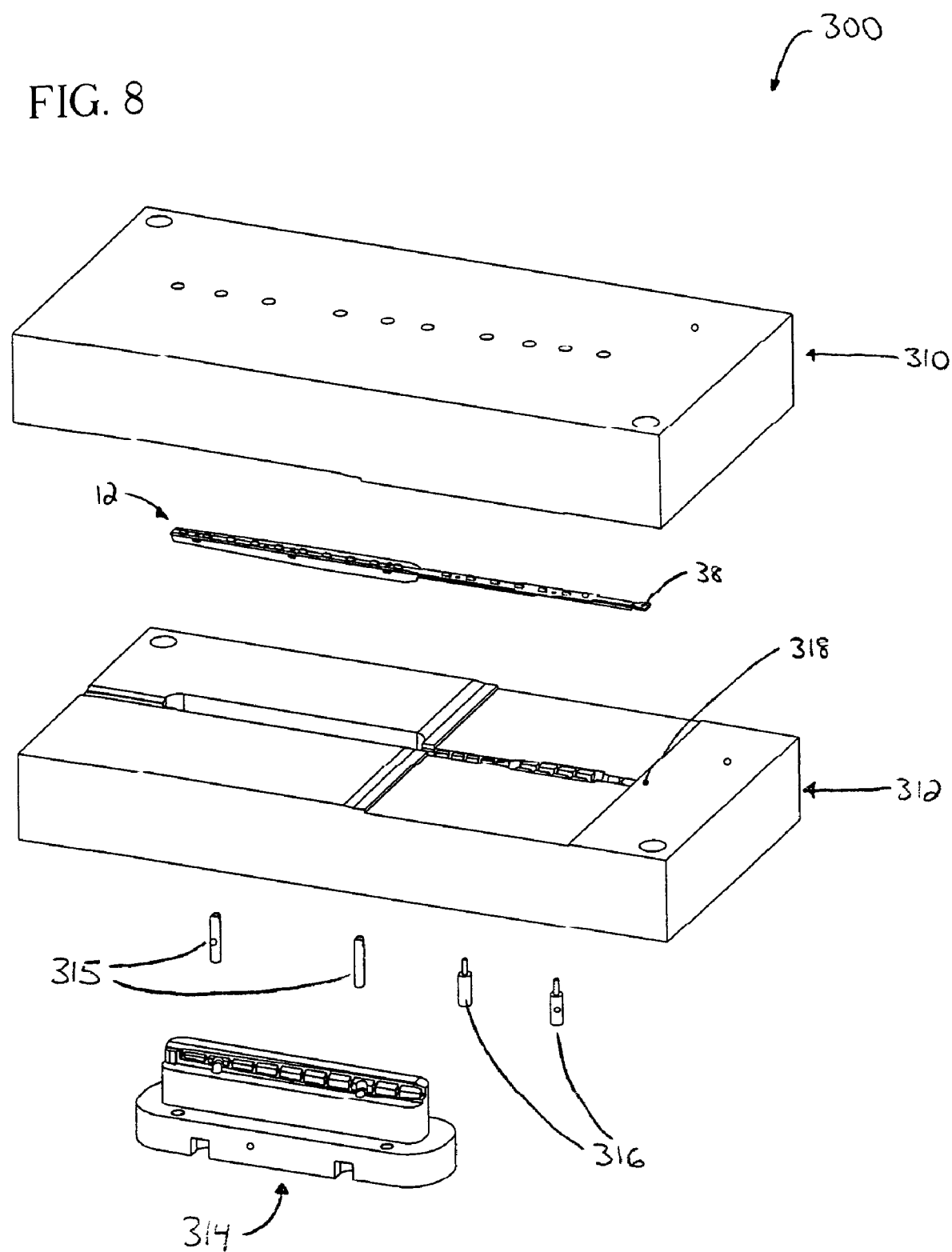
FIG. 8 is an exploded view of the injection molding process according to a preferred embodiment of the present invention.
Figure 9:
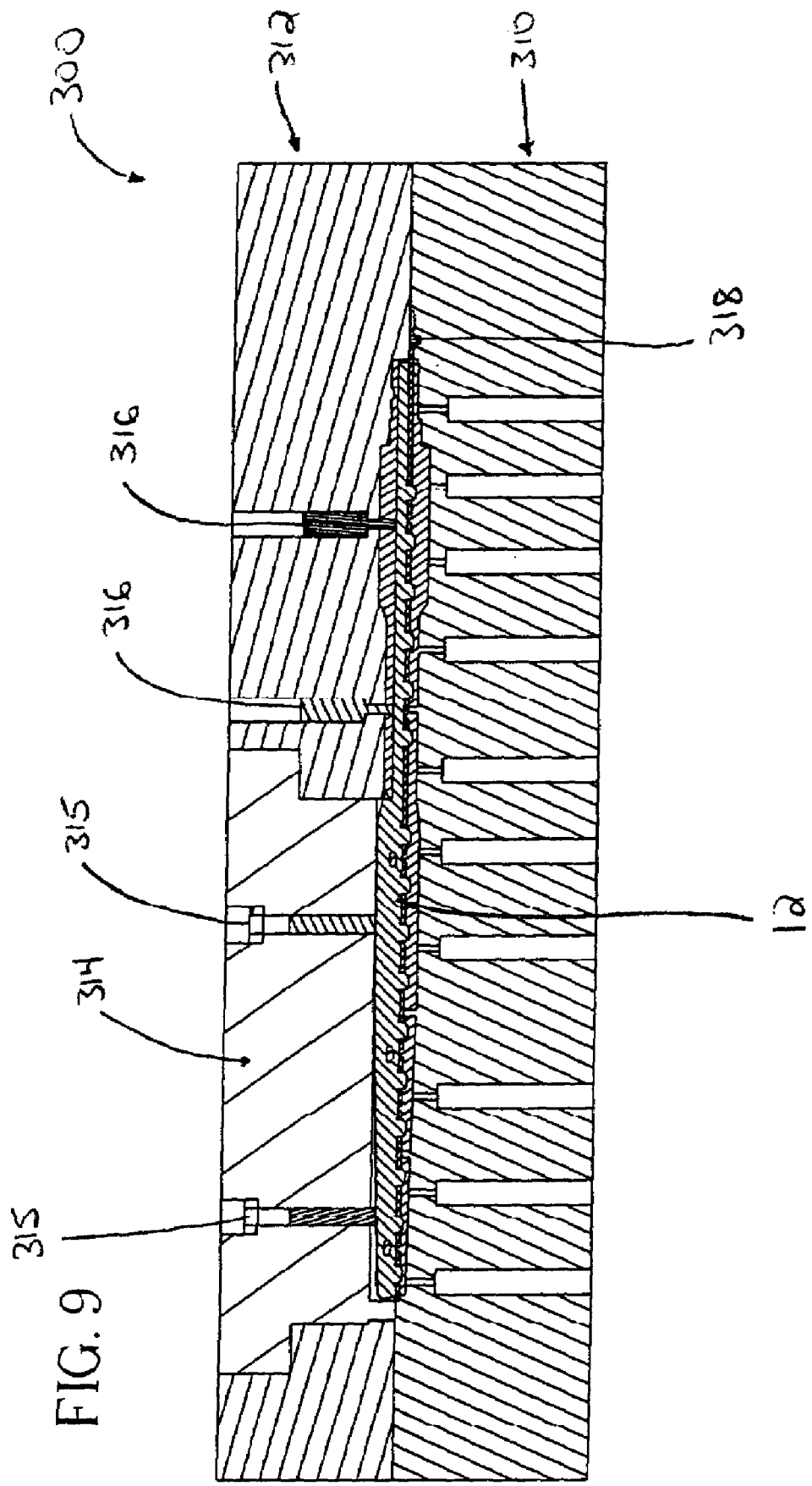
FIG. 9 is a side cross sectional view of the injection molding process according to a preferred embodiment of the present invention.

Another aspect of the present invention relates to a method for forming an orthopedic reamer according to the present invention. A preferred embodiment of the instruments utilized in the process is shown in FIGS. 8 and 9. The preferred method of injection molding, as shown in the figures, is accomplished using a mold 300, including a first mold plate 310, a second mold plate 312, a mold insert 314, and pins 316. However, it is contemplated that other instruments and method steps can be utilized to injection mold reamer 10 in accordance with the present invention. These instruments and processes are known to those of ordinary skill in the art. Similarly, other processes for forming polymeric body portion 14 around cutting portion 12 can be performed.

The method according to this aspect of the present invention includes the step of providing one or more non-polymeric sections to form a cutting portion 12 as disclosed above. In this step, it is contemplated that a cutting portion 12 can be any configuration which allows for the formation of a reamer suitable for reaming a bone canal. For example, as discussed above, a cutting portion 12 can be provided that includes any number of cutting edges 26 for cutting the bone or that includes any shaped tip surface 30 for making initial contact with the bone. Additionally, a cutting portion 12 can be provided which includes any number of cutting components 13.

The method according to this aspect of the present invention also includes the step of molding a polymer material over the cutting portion 12 to create a reinforcing body portion 14. This step is accomplished by utilizing any molding process known to one of ordinary skill in the art. For example, in a preferred embodiment, the polymer material may be injection molded over the cutting portion 12. In the preferred embodiment as shown in FIG. 9, this injection molding step is accomplished while utilizing mold 300. An assembled cutting portion 12 (i.e.—with cutting components 13*a* and 13*b* connected) is placed into a space between first mold plate 310 and second mold plate 312. This space is formed by partial voids located on both mold plates 310 and 312. Assembled cutting portion 12 is first engaged with second mold plate 312. It is contemplated that mold alignment tab 38 is operatively engaged with a guide pin 318 located on second mold plate 312. This assures that cutting portion 12 is aligned correctly in mold 300 and remains in this position during the molding process. A mold insert 314 is thereafter connected to second mold plate 312 with slotted pins 315 permanently seated in insert 314. Slotted pins 315 capture a single blade portion in slots formed on each slotted pin 315. Thereafter, pins 316 are engaged with mold insert 314 and second mold plate 312 to hold the pieces together. Mold insert 314 allows for mold 300 to be more easily fabricated by preventing the need for an entire void to be created on mold plate 312. Further, mold insert 314 aids in holding cutting portion 12 in mold 300. In the preferred method, sharp edges 27*a*, 27*b*, and 27*c* fit snuggly in slots created by the elements of mold 300, so as to keep polymer material from forming thereon.

With cutting portion 12 located between first mold plate 310 and second mold plate 312, a polymer material is injected into the mold. The shape of the aforementioned voids on first mold plate 310 and second mold plate 312 dictates the shape of polymer body 14 formed around cutting portion 12. In a preferred embodiment, polymeric body 14 includes forming ribbed sections 44 on body portion 14. As mentioned above, these ribs allow the polymeric material to cool evenly and prevent shrinkage in the sections of polymeric body 14. Additionally, polymeric body 14 includes forming a geometric shape that can be utilized as a quick connection 46. Nevertheless, this step of injection molding should be performed so as to substantially cover the cutting portion 12 with a polymer material, but allowing cutting edges 27 to remain uncovered. Subsequent to the injection molding step, the newly applied polymeric material is allowed to cool and harden. Thereafter, molding plates 310 and 312 are separated, and reamer 10 is removed therefrom. Optionally, pins 316 may be removed to separate mold insert 314 from second mold plate 312. In a preferred embodiment, sharp edges 27*a*, 27*b*, and 27*c* are sharpened prior to the molding process. The sharpening of the edges is accomplished by providing a rake angle, i.e. a higher side being a leading edge in the direction of the cut and a lower side being a trailing edge. Typically the sharp edges are provided with a rake angle of approximately five degrees, but can be different values. It is contemplated that sharpening of the edges can be done subsequent to the formation of polymeric material around reamer 10, by any process known in the art for forming a sharp edge on a metallic portion.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic reamer comprising:
   a non-polymeric elongate cutting portion having multiple non-polymeric cutting components assembled together each having at least one elongate bone cutting surface thereon, and an elongate outwardly facing surface extending continuously along all of a length of said cutting portion; and
   a polymeric body portion covering at least a portion of the outwardly facing surface of said cutting portion continuously along all of the length of said cutting portion,
   wherein said polymeric body portion provides support to said non-polymeric elongate cutting portion and keeps the multiple non-polymeric cutting components assembled together, and the at least one bone cutting surface is not covered by said polymeric body portion.

2. The orthopedic reamer according to claim 1, wherein the number of bone cutting surfaces numbers from two (2) to six (6).

3. The orthopedic reamer according to claim 1, wherein said reamer has a generally circular cross section.

4. The orthopedic reamer according to claim 1, wherein said reamer has a generally triangular cross section.

5. The orthopedic reamer according to claim 1, further comprising a connect fitting at a first end thereof for facilitating connection to a machine.

6. The orthopedic reamer according to claim 5, wherein the machine is a drill.

7. The orthopedic reamer according to claim 1, wherein said non-polymeric cutting portion is constructed from a metal.

8. The orthopedic reamer according to claim 1, wherein said polymeric body portion further comprises polymeric ribs.

9. The orthopedic reamer according to claim 1, wherein said non-polymeric cutting portion comprises two cutting components.

10. The orthopedic reamer according to claim 1, wherein said non-polymeric cutting portion comprises four cutting components.

11. The orthopedic reamer according to claim 1, wherein said non-polymeric cutting portion further comprises at least one aperture for allowing said polymeric body section to be molded therethrough.

12. The orthopedic reamer according to claim 1, wherein the cutting surfaces further include chip breakers.

13. The orthopedic reamer according to claim 1, further including a metal core that runs the entire length of said reamer.

14. The orthopedic reamer according to claim 1, wherein said non-polymeric elongate cutting portion includes a section entirely covered by said polymeric body portion.

15. An orthopedic reamer comprising:
a body having at least two elongate metal blade portions retained together, each blade portion having at least one elongate outwardly extending cutting surface, said blade portions oriented at an angle to adjacent blade portions forming an elongate outwardly facing recess therebetween and a polymeric support at least partially filling said outwardly facing recess between said blades, said polymeric support leaving said cutting surfaces exposed, wherein said outwardly facing recess extends continuously along all of a length of said cutting surface and said polymeric support fills said outwardly facing recess, and wherein said polymeric support provides support to said body and keeps said at least two elongate metal blade portions retained together.

16. The reamer as set forth in claim 15 wherein each of the blades are made of an elongated metal plate having a pair of longitudinally extending edges, a first edge having the cutting surface and a second edge including an attachment element for engaging said adjacent blade portions.

17. The reamer as set forth in claim 16 wherein an elongated recess extends between adjacent blades and said polymer extends along said recess as a series of webs.

18. The reamer as set forth in claim 15 wherein the blades are tapered towards a first end of said body.

19. The reamer as set forth in claim 15 wherein the number of cutting surfaces numbers from two (2) to six (6).

20. The reamer as set forth in claim 15 further comprising a connect fitting for facilitating connection to a machine.

21. The reamer as set forth in claim 15, wherein said body includes a section entirely covered by said polymeric support.

22. An orthopedic reamer comprising:
a body having
at least two elongate metal blade portions retained together, each blade portion having at least one elongate outwardly extending cutting surface, said blade portions oriented at an angle to adjacent blade portions forming an elongate outwardly facing recess therebetween, wherein each of the blades are made of an elongated metal plate having a pair of longitudinally extending edges, a first edge having the cutting surface and a second edge including an attachment element for engaging said adjacent blade portions; and
a polymeric support at least partially filling said outwardly facing recess between said blades, said polymeric support leaving said cutting surfaces exposed, wherein said outwardly facing recess extends along substantially all of a length of said cutting surface and said polymeric support extends along said outwardly facing recess as a series of webs, and wherein said polymeric support provides support to said body and keeps said at least two elongate metal blade portions retained together.

* * * * *